United States Patent
Heigl et al.

(10) Patent No.: US 9,943,369 B2
(45) Date of Patent: Apr. 17, 2018

(54) FIXATION SYSTEM FOR AN IMAGE REGISTRATION MATRIX

(75) Inventors: Rupert Heigl, Markt Schwaben (DE); Norman Plassky, Erfurt (DE); Brian Vasey, Munich (DE); Stephan Karasz, Feldkirchen (DE)

(73) Assignee: Brainlab AG, Munich (DE)

( * ) Notice: Subject to any disclaimer, the term of this patent is extended or adjusted under 35 U.S.C. 154(b) by 140 days.

(21) Appl. No.: 14/000,529

(22) PCT Filed: Mar. 4, 2011

(86) PCT No.: PCT/EP2011/053281
§ 371 (c)(1),
(2), (4) Date: Aug. 20, 2013

(87) PCT Pub. No.: WO2012/119634
PCT Pub. Date: Sep. 13, 2012

(65) Prior Publication Data
US 2013/0331688 A1  Dec. 12, 2013

(51) Int. Cl.
| | |
|---|---|
| A61B 5/05 | (2006.01) |
| A61B 19/08 | (2006.01) |
| A61B 5/055 | (2006.01) |
| A61B 6/03 | (2006.01) |
| A61B 46/10 | (2016.01) |

(Continued)

(52) U.S. Cl.
CPC ............ *A61B 19/081* (2013.01); *A61B 5/055* (2013.01); *A61B 6/032* (2013.01); *A61B 46/10* (2016.02); *A61B 90/14* (2016.02); *A61B 2034/2055* (2016.02); *A61B 2090/3954* (2016.02); *A61B 2090/3983* (2016.02); *A61B 2090/3995* (2016.02)

(58) Field of Classification Search
USPC .......................................... 600/424
See application file for complete search history.

(56) References Cited

U.S. PATENT DOCUMENTS 3,982,307 A * 9/1976 Smith .................... A44B 99/00
   24/543
4,024,870 A * 5/1977 Sandel ................. A61B 17/282
   294/118

(Continued)

OTHER PUBLICATIONS

International Search Report for International Application No. PCT/EP2011/053281 dated Nov. 28, 2011.

*Primary Examiner* — Joel F Brutus
(74) *Attorney, Agent, or Firm* — Tucker Ellis LLP

(57) ABSTRACT

The invention relates to a fixation system for attaching a medical image registration matrix (40) to a patient holder (2) which is to be covered by a sterile drape (10), wherein the fixation system comprises at least one fixation set (L, R) comprising a lower part (6) which is adapted to be connected to the patient holder (2) and an upper part (26) which is adapted to be connected to the registration matrix (40) or one of its supporting elements, wherein: the lower and upper parts (6, 26) can be connected to each other by a connector (25) which does not penetrate the drape (10); the lower and upper parts (6, 26) comprise mutually engageable profiled interfaces (8, 28) which are formed so as to accommodate and clamp the drape (10) between them; and wherein the profiled interfaces (8, 28) fit together over a continuous zone of engagement.

19 Claims, 2 Drawing Sheets

(51) Int. Cl.
 *A61B 90/14* (2016.01)
 *A61B 90/00* (2016.01)
 *A61B 34/20* (2016.01)

(56) References Cited

U.S. PATENT DOCUMENTS

| | | | |
|---|---|---|---|
| 5,052,396 | A | 10/1991 | Wedel et al. |
| 5,396,905 | A * | 3/1995 | Newman ............... A61B 19/08 128/853 |
| 5,423,832 | A | 6/1995 | Gildenberg |
| 5,971,997 | A | 10/1999 | Guthrie et al. |
| 6,142,937 | A | 11/2000 | Lemcke et al. |
| 6,198,961 | B1 | 3/2001 | Stern et al. |
| 6,471,172 | B1 * | 10/2002 | Lemke .................... A61B 19/26 248/125.7 |
| 2001/0007918 | A1 | 7/2001 | Vilsmeier et al. |
| 2002/0161446 | A1 * | 10/2002 | Bryan et al. ............... 623/17.15 |
| 2008/0177173 | A1 | 7/2008 | Deffenbaugh et al. |
| 2008/0221520 | A1 | 9/2008 | Nagel et al. |
| 2008/0269599 | A1 * | 10/2008 | Csavoy et al. ................ 600/426 |
| 2009/0143684 | A1 | 6/2009 | Cermak et al. |
| 2009/0308400 | A1 | 12/2009 | Wilson et al. |

* cited by examiner

FIXATION SYSTEM FOR AN IMAGE REGISTRATION MATRIX

This application is a national phase of International Application No. PCT/EP2011/053281 filed Mar. 4, 2011 and published in the English language.

The present invention relates to a fixation system for attaching a medical image registration matrix to a patient holder which is to be covered by a sterile drape. The field of application for the present invention is that of integrating navigated surgery and intra-operative imaging. The invention is preferably used for integrating a neurosurgical treatment and magnetic resonance imaging (MRI), but is also applicable to other forms of treatment or surgery in connection with various medical imaging techniques such as computed tomography (CT), etc.

In such surgical procedures, i.e. in image-guided surgery or navigationally assisted surgery using a medical navigation and tracking system, at least one non-sterile patient scan and at least one sterile scan of the patient are typically conducted. The term "sterile scan" implies that the patient's treatment area must be kept sterile during this scan which is typically an intra-operative imaging procedure, wherein the sterile field must be prevented from becoming contaminated. Precautions for maintaining sterility must be taken, for example the use of a (second) sterile drape to cover the sterile treatment field during the scanning process, because large imaging devices such as MRI scanners or CT scanners cannot be sterilised.

The patient must be scanned together with a so-called registration matrix in order to enable a correlation between the co-ordinate system of the navigation system of the image-guided surgery system and the co-ordinate system of the imaging device to be established. The registration matrix bears multiple markers which can be identified in the scanned image data (for example, MR markers), and tracking markers are usually provided in a fixed positional relationship with the matrix, in order for three-dimensional volume tracking (surgical navigation) to be integrated.

Figure 2:
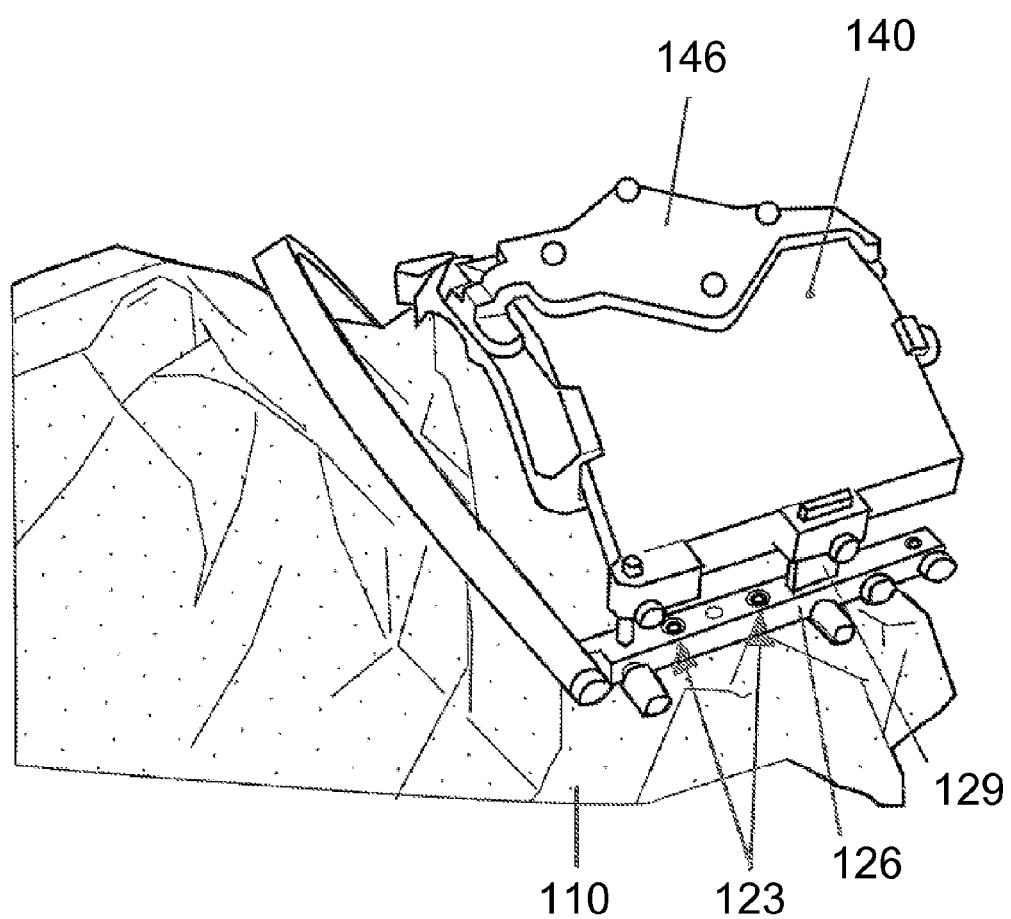

FIG. 2 shows an example of an attachment system in accordance with the prior art, wherein the matrix has been given the reference number 140, and a holder 146 which bears tracking markers (not provided with reference numbers of their own in FIG. 2) is fixedly attached to the matrix 140.

The exact geometric configuration of the tracking markers and imaging markers is known or calibrated in the navigation system and used to automatically register the image data. It is mandatory to prevent any movement of the registration matrix with respect to the part of the patient's body—in the present examples, the patient's skull. The matrix is therefore usually attached to a head holder device which is fixed to the patient's skull via skull pins.

After a first, pre-operative and non-sterile scan, a drape is installed at the interface between the head holder and the supporting elements of the registration matrix. In FIG. 2, the upper part 126 of the fixation system is shown above the drape 110. The lower part of the fixation system according to the prior art cannot be seen in FIG. 2, but it can be seen that the bar-like upper part 126 has screw connections 123 via which it is fixed in a single predetermined position on the corresponding lower part. Screws are set and tightened in threaded bores provided in the upper part 126 and its corresponding lower part, in order to achieve a rigid fixation.

During this installation procedure, the drape 110 must be cut at several positions within the connection locations, which always risks impairing sterility. In order to avoid a loss of sterility, the interfaces between the upper part 126 and its corresponding lower part usually exhibit a large contact surface in order to seal the area around the positions where the drape has been penetrated. For this reason, no adjustment or removal of the interface or parts of it is allowed during surgery. However, the registration matrix must be temporarily removed in order to perform the surgical treatment. To enable this, an additional interface is provided between the upper part 126 and the registration matrix 140, namely the interface 129 which can only be adjusted in height and requires a complex adjustment procedure which necessitates access to both sides of the matrix.

The image data are usually acquired once immediately before the surgical procedure in a non-sterile environment, whereas subsequent scans (intra-operative scans) are implemented in a sterile environment. Accordingly, the whole installation procedure must be repeated prior to each scan. Because the integration hardware devices have to be provided on both the non-sterile and sterile side, it is mandatory to have two sets of each of the devices provided for the respective surgical procedure. Such integration hardware usually consists of the tracking array 146, the matrix 140 and the supporting elements and is also required when the image data are subsequently used in surgical navigation. In the embodiment according to the prior art, all the devices and instruments which must be installed prior to the scanning procedure have to be carefully placed and adjusted in position so as to avoid blocking too large a volume in view of the relatively small apertures of imaging devices such as MRI scanners. Accordingly, the clinical personnel try to install all such devices and instruments as close as possible to the part of the patient's body, and the integration hardware does not usually offer a sufficient degree of freedom and adjustability.

The fixation system of the present invention comprises at least one fixation set comprising a lower part which is adapted to be connected to the patient holder and an upper part which is adapted to be connected to the registration matrix or one of its supporting elements. To this extent, the system of the present invention corresponds to the design of the prior art.

It is the object of the present invention to provide a fixation system for attaching a medical image registration matrix to a patient holder which is to be covered by a sterile drape, wherein at least one of the problems discussed above with respect to the prior art is overcome by the system of the present invention. The present invention in particular aims to prevent any loss of sterility caused by fixing the matrix and/or to provide an easy-to-handle and reliable fixation system. This object is achieved by a fixation system in accordance with claim 1. The sub-claims define advantageous embodiments of the invention.

The fixation system in accordance with the present invention exhibits the following features:
- the lower and upper parts can be connected to each other by a connector which does not penetrate the drape;
- the lower and upper parts comprise mutually engageable profiled interfaces which are formed so as to accommodate and clamp the drape between them; and
- the profiled interfaces fit together over a continuous zone of engagement.

In other words, the present invention ensures on the one hand that the upper and lower parts are stably and securely fixed, by using non-planar, i.e. profiled interfaces between them, while on the other hand allowing the user a certain freedom with regard to the position at which said interfaces are connected, by avoiding distinct or discrete localised engagement positions, i.e. by instead providing a non-incremental (continuous) positioning or engagement zone.

One major advantage of this design is that a user is not required to isolate one exact position of engagement between the lower and upper parts and can thus easily fix the registration matrix or establish a situation in which it is easily fixed. This can substantially reduce the installation time and the scope for making mistakes during the installation procedure. On the other hand, profiled interfaces still provide some guidance in the fixing and/or aligning process, but can be designed in such a way that they can easily accommodate one, two or more drapes at the interface.

The zone of engagement can be a length of engagement, wherein the profiled interfaces could then enter into engagement at any position along said length of engagement, such that the possible engagement positions would extend along a continuous path.

In one embodiment, the zone of engagement offers one degree of freedom in one direction of extension along the lower and/or upper part(s) or their interfaces. As mentioned above, this one direction of extension can in particular be a degree of freedom along the length of the lower and/or upper part(s) or their interfaces. It is this degree of freedom which allows the user a certain freedom when for example positioning the upper part on the lower part.

In the zone of engagement, the interfaces of the lower and/or upper parts can allow a degree of play in the engagement area which is large enough to accommodate the thickness of at least one and preferably two or more sterile drapes. This degree of play can easily be adapted to the specific application of the matrix, such that it can on the one hand provide an effective positioning aid, while on the other hand accommodating exactly the number of drapes necessary for said specific application. An MR scanning process would for example require two drapes in its intra-operative mode, and the play between the interfaces in the engagement area can be adapted to conform to this restriction.

In one preferred embodiment, one of the lower parts and upper parts comprises a rail and the other of the lower parts and upper parts comprises a rail-engaging, in particular rail-spanning profile, wherein one of the rail or the rail-engaging profile has a length which substantially exceeds the length of the other of the rail or the rail-engaging profile.

The rail can comprise two co-extending rail parts which are connected by a mounting element, in particular a pivotable mounting element, which in particular comprises a lockable pivot. The mounting element can be used to mount the rail on the patient holder, while pivots which are in particular lockable pivots facilitate fixing the matrix, i.e. initially placing it, but still rigidly fix it at the end.

In accordance with one embodiment of the present invention, the fixation system comprises a matrix support which directly or indirectly bears the matrix and is attached to at least one fixation set, such that the matrix can be mounted on the support which can in turn be mounted in place via the fixation set. It is of course also possible to provide two fixation sets which are to be arranged on opposite portions of the patient holder, wherein the lower part or rail of one fixation set comprises a lockable pivot, while the lower part or rail of the other fixation set comprises a free pivot. This arrangement makes it easier for the user to place and connect the matrix and its supporting elements.

As mentioned above, the fixation system can comprise two fixation sets which can in turn comprise:

two upper parts which are adapted to be attached to both ends of a bridge element which forms the matrix support; and two lower parts which are adapted to be mounted, in particular pivotably, on the two end portions of a head ring being used as the patient holder.

The matrix support, which is in particular formed as a bridge element, is described here in various embodiments as a feature which further develops the present invention into even more advantageous forms. However, it should be noted in this respect that the features described here in connection with the matrix support, the bridge element and its embodiments represent an inventive aspect in their own right and can also be embodied on a matrix support system which is not constrained by the connection system for the lower and upper parts of the fixation system as described above.

The matrix support, in particular the bridge element, can comprise a template for supporting or accommodating the matrix, in particular for accommodating reference portions of the matrix. This embodiment ensures that the reference portions which bear the markers to be imaged are scanned at their correct and predetermined locations.

In accordance with one preferred aspect of the invention, the matrix support or bridge element and/or the template are substantially transparent and in particular made of a substantially transparent and preferably lightweight plastic material. They can be adjustably connected to at least one of the fixation sets via adjustment elements for controlling the height and/or width and/or rotational position of the matrix support or bridge element.

The upper and lower parts can be connected by being fixed to each other by operating the connector, such that they engage each other in a frictional fit and/or a positive fit. It is possible in embodiments for said connector to clamp the upper and lower parts together, without of course penetrating any drape material situated between the upper and lower parts. In such a clamping action, the connector may well clamp a portion of the drape too, at least on one side of the clamping brace. The connector is preferably a quick-release fastener, in particular a snap closure.

The invention will now be described in more detail by referring to a particular embodiment and the attached FIG. 1 which shows a fixation system according to the present invention installed on a head clamp. It should be noted that each of the features of the present invention as referred to here can be implemented separately or in any expedient combination. As mentioned above, FIG. 2 shows an embodiment in accordance with the prior art, the components of which have already been described in the introductory portion of the present specification.

Figure 1:
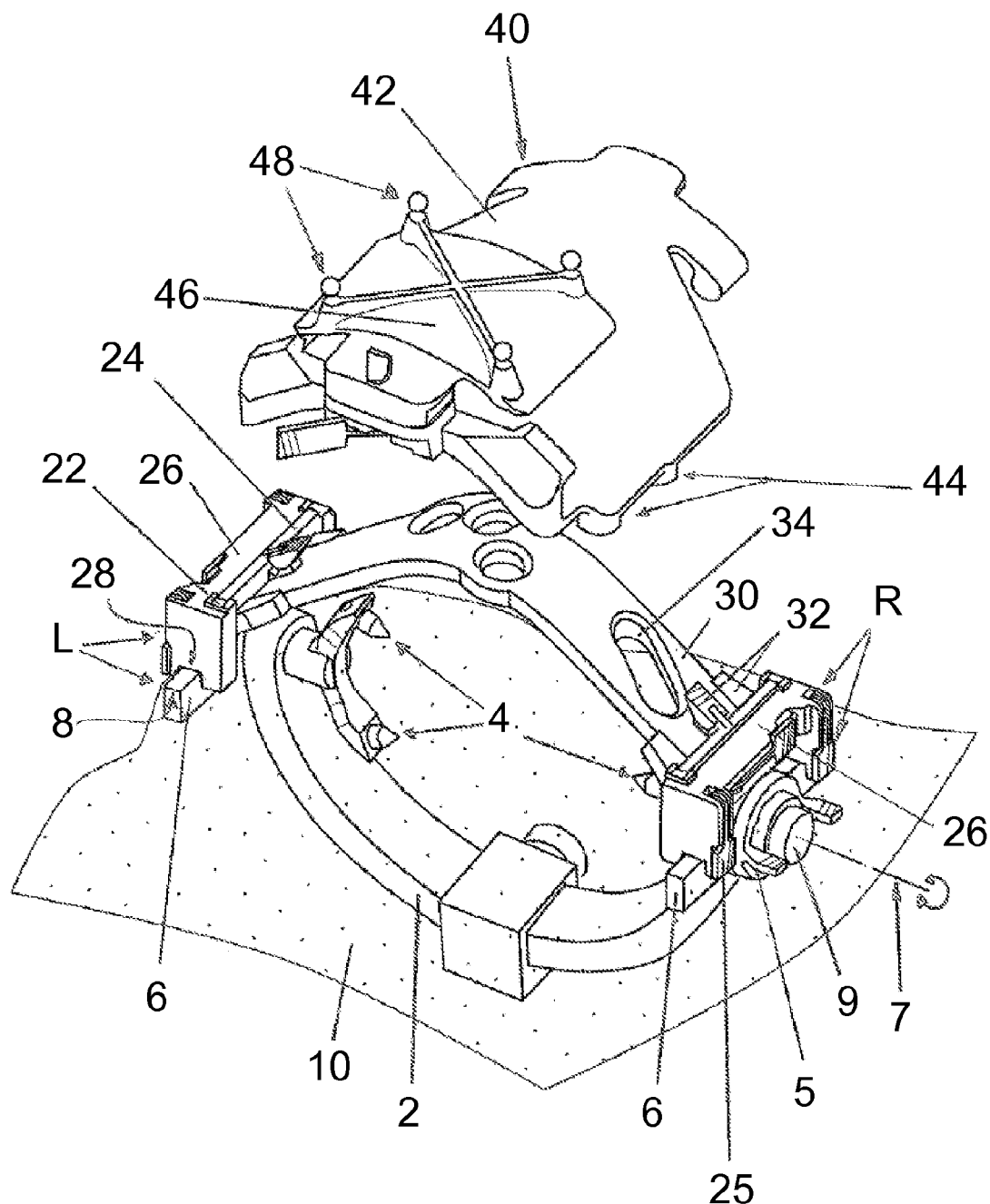

As shown in FIG. 1, the fixation system in accordance with the present invention is used to connect an MRI matrix 40 to a head clamp 2. The elements shown in FIG. 1 can be divided into two categories, namely those arranged below a sterile drape 10 and those arranged above the drape 10. The elements arranged below the drape have been given reference numbers below 10, while the reference numbers higher than 10 indicate elements which are situated above the drape.

The elements below the drape 10 are the aforementioned head clamp 2, its skull pins 4, the fixation screw 5 for fixing the right-hand side rail 6 to the right-hand side of the head clamp 2 at its end portion, and the interface 8 of the rail 6 which in the present embodiment is formed as a rectangular end portion. The rails 6 have two co-extending end portions which are connected to each other by a mounting element which would be annular in the present embodiment and cannot be seen in FIG. 1. Using its mounting ring, the rail 6 is pushed onto a fixation extension 9 on which it can pivot freely until it is fixed using the fixation screw 5. At the other end portion of the head clamp 2, the rail 6 is mounted in a similar manner but remains freely pivotable.

The above-mentioned elements which remain below the drape can be identified in the drawing by the fact that they are covered by the dots of the dotted drape, whereas the elements above the drape do not exhibit such dots.

The reference signs L and R indicate the two fixation sets, i.e. a left-hand fixation set and a right-hand fixation set, respectively. They each comprise a rail 6 below the drape 10 and an upper part 26 which is arranged above the drape 10.

The elements above the drape include two upper parts 26 comprising interfaces 28 which are designed as concave rectangular (angled U-shaped) portions for accommodating the rectangular, convex upper end portion of the interface 8, with a degree of play in between for the drape 10. A bridge or template 30 is fastened to both the upper parts 26 via linearly adjustable guides 32, and a slider 24 can be and is slid into a retainer guide 22 of the upper part 26 in a linearly adjustable manner. The bridging portion of the bridge or template 30 comprises openings 34 which are designed to accommodate extensions 44 on the underside of the MRI matrix 40, such that the matrix 40 can be placed onto the template 30 in a positionally determined way. The matrix 40 comprises a matrix body 42, wherein a tracking reference holder 46 comprising four tracking references or markers 48 is placed on the upper side of the matrix body 42, again in a positionally determined manner.

As mentioned above, most of the known problems in the prior-art solutions relate to the drape interface of the registration matrix. The present invention offers a unique interface which is suitable for rigidly installing the registration matrix but does not penetrate the drape. Additionally, the interface has been designed to allow multiple sets of drapes to be installed. These features enable a single, non-sterile device to be used, thus avoiding the complex procedure involved when using two sets of hardware. The non-sterile matrix can be used at any time, and the drapes can be installed when and where necessary in order to maintain the sterile field.

In order to achieve this, the rails 6 in the embodiment of FIG. 1 are installed at the end portions of the head clamp 2 and exhibit a rectangular shape and a generous length. The rail 6 of the right-hand fixation set R can be aligned such that it is rotatable about the axis 7, but then fixed at the desired angle by the fixation screw 5. Since fixing said rail in this way leaves the matrix and its supporting elements with no other rotational degrees of freedom, the rail 6 of the left-hand fixation set L can be left freely rotatable and will be fixed by its opposing counterpart when installation is complete.

If an intra-operative scan is to be carried out, at least one drape can be placed over the rails 6 and the patient. At this stage, the patient may already have been draped once, such that the rails 6 may then be covered by two drapes.

However, it is still then possible and practical to place the upper parts 26 onto the drape-covered rails 6, due to their easily identifiable shape and generous length, such that a user can easily locate the interfaces beneath the (usually non-transparent) drapes. The user is not required to align the two parts of the interface in an exact position beneath the drape, because any position on the rails 6 is suitable for coupling them to the upper parts 26. The concave, U-shaped opening or interface 28 is wide enough and provides sufficient clearance or play for the width of the rail and one or more sets of drapes.

Each upper part 26 comprises connectors 25 which in the present example are embodied as quick-release levers. Once actuated, these levers 25 press the upper parts 26 outwards, such that the upper parts 26 are fixed on the rails 6 in a frictional fit. In other embodiments, the connectors 25 could also automatically clamp the rails 6 when pushed onto them.

Flexible portions or springs can be arranged on the interfaces in order to clamp the drape gently and without penetrating it. Such flexible elements can also compensate for different drape thicknesses.

A lightweight template (bridge) 30 is mounted between the fixation sets L and R. It is small and preferably transparent, and since it is light in weight and rotationally fixed on one side (R) only, it can be easily installed and adjusted with little operating force and without the typical problems caused by the heavy registration matrix according to the prior art with its attached receiving coil and tracking array. The template 30 comprises openings 34 which allow the matrix 40 to be exactly aligned by corresponding to the shape of lower extensions 44 on the underside of the matrix 40. In specific embodiments, the template and the matrix could be integrated with each other and/or also with the fixation sets. The rather small opening of an MRI scanner is important to note in this respect: for which reason the user may try to position the hardware as close as possible to the patient's head without touching the patient, and this installation step is significantly easier if the template is transparent and lightweight.

Either the template 30 or the matrix 40 can comprise a feature which is capable of locking the matrix 40 rigidly to the template 30.

The extensions 44 on the matrix 40 comprise multiple MR markers which can be identified in the MR image data. The tracking array, which includes the tracking reference holder and the tracking references or markers 48, has in combination with the MR marker array on the extensions 44 an exact geometric configuration which allows the image data to be automatically registered in a medical navigation system using a tracking system.

Any combination of the matrix, the template and the fixation sets is in principle possible. It can even be appropriate to integrate at least one fixation set and the template and provide them as a monolithic combination. The rail on the left-hand side, together with the left-hand fixation set, can in principle be optional, but if they are provided, they are preferably free in terms of rotation, in order to prevent a statically over-determined state which would incur additional internal loads on the elements. Such an approach enables a fast and easy setup involving only one upper part and one rail. Once the setup and alignment of the template or the matrix is complete, the second upper part can be attached to the second rail. The linear guide which couples the upper parts and the template does not require the user to access the entire apparatus from the other side.

In order to allow the height to be flexibly adjusted, the upper part and the matrix and the template are preferably not integrated, as shown in the example of FIG. 1; instead, a linear guide 32 and fixation mechanism are provided on these components. The second upper part 26 on the left-hand side is installed so as to compensate for the influence of the weight of the registration matrix 40 and its attachments. This second fixation set is connected after the template 30 has been adjusted in terms of its height and rotational orientation. The left-hand fixation set L does not require adjustment and can be installed without having to access the setup from the other side, as mentioned above. In order to avoid any residual stress resulting from this installation at two ends, the second rail 6 on the left-hand side is left free in terms of rotation, as mentioned above.

Features are also provided which allow width tolerances on the head holder to be compensated for. This function can be fulfilled by the linear guide 32, which in turn can also prevent the influence of any potential spread of the head clamp 2 if a fixation force exerted by the skull pins 4 is increased. The height can easily be adjusted using the slider 24 and its retainer guide 22.

The invention claimed is:

1. A fixation system for attaching a medical image registration matrix to a patient holder which is to be covered by a sterile drape and has first and second ends opposite one another, wherein the fixation system comprises two fixation sets, wherein one of the two fixation sets is arranged on the first end of the patient holder and another of the two fixation sets is arranged on the second end of the patient holder laterally spaced from the one of the two fixation sets arranged on the first end, the two fixation sets comprising:
    two upper parts which are adapted to be attached to both ends of a bridge element which forms a matrix support; and
    two lower parts which are adapted to be mounted on two end portions of a head ring forming the patient holder, wherein:
    the two lower parts and the two upper parts can be releasably connected to each other;
    one of the two lower parts and two upper parts comprise two longitudinally extending co-extending rails, and another of the two lower parts and the two upper parts comprise two longitudinally extending rail-engaging profiles, the two longitudinally extending co-extending rails and the two longitudinally extending rail-engaging profiles being formed so as to allow the two upper parts being placed onto the two lower parts covered by the sterile drape in a direction that is perpendicular to an extension of the two longitudinally extending co-extending rails, the two longitudinally extending co-extending rails and the two longitudinally extending rail-engaging profiles being formed to accommodate and clamp the sterile drape between them without penetrating the sterile drape; and
    the two longitudinally extending co-extending rails and the two longitudinally extending rail-engaging profiles fit together over a continuous zone of engagement, the continuous zone of engagement extending over a length of the two longitudinally extending co-extending rails and/or the two longitudinally extending rail-engaging profiles, and allowing the two longitudinally extending rail-engaging profiles to engage the two longitudinally extending co-extending rails at an arbitrary position along the length of the two longitudinally extending co-extending rails and/or the two longitudinally extending rail-engaging profiles, thereby allowing the two lower parts and the two upper parts to be connected to each other at the arbitrary position.

2. The fixation system according to claim 1, wherein the continuous zone of engagement offers one degree of freedom in one direction of extension along the two lower parts and/or the two upper parts or their interfaces.

3. The fixation system according to claim 2, wherein the continuous zone of engagement offers one degree of freedom along a length of the two lower parts and/or the two upper parts or their interfaces.

4. The fixation system according to claim 1, wherein in the continuous zone of engagement, interfaces of the two lower parts and/or the two upper parts allow for space in their engagement area to accommodate a thickness of at least one sterile drape.

5. The fixation system according to claim 1, wherein a fixation set comprises a flexible material or flexible element on an interface of at least one of the two lower parts and the two upper parts.

6. The fixation system according to claim 1, wherein one of the two longitudinally extending co-extending rails or one of the two longitudinally extending rail-engaging profile has a length that exceeds a length of another of the two longitudinally extending co-extending rails or the two longitudinally extending rail-engaging profiles.

7. The fixation system according to claim 6, wherein the two longitudinally extending co-extending rails are connected by a mounting element.

8. The fixation system according to claim 7, wherein the mounting element is a pivotable mounting element that comprises a lockable pivot.

9. The fixation system according to claim 1, wherein the matrix support directly or indirectly bears the medical image registration matrix and is attached to at least one of the two fixation sets.

10. The fixation system according to claim 9, wherein the matrix support or bridge element comprises a template for supporting or accommodating the medical image registration matrix.

11. The fixation system according to claim 9, wherein the matrix support or bridge element and/or the template are transparent.

12. The fixation system according to claim 9, wherein the matrix support or bridge element and/or the template are adjustably connected to at least one of the two fixation sets via adjustment elements for controlling the height and/or width and/or rotational position of the matrix support or bridge element.

13. The fixation system according to claim 1, wherein one of the two longitudinally extending co-extending rails comprises a lockable pivot, and one of the two longitudinally extending co-extending rails comprises a free pivot.

14. The fixation system according to claim 1, wherein the two upper parts and the two lower parts are configured to be connected by being fixed to each other by operating a connector, such that they engage each other in a frictional fit and/or a positive fit.

15. The fixation system according to claim 14, wherein the connector is a quick-release fastener.

16. The fixation system according to claim 1, wherein the two lower parts are pivotably mounted on two end portions of a head ring forming the patient holder.

17. The fixation system according to claim 1, wherein the two longitudinally extending rail-engaging profiles have respective interfaces having a concave rectangular portion and the two longitudinally extending co-extending rails have respective interfaces having a rectangular convex end portion.

18. A fixation system for attaching a medical image registration matrix to a patient holder which is to be covered by a sterile drape and has first and second ends opposite one another, wherein the fixation system comprises two fixation sets, wherein one of the two fixation sets is arranged on the first end of the patient holder and another of the two fixation sets is arranged on the second end of the patient holder laterally spaced from the one of the two fixation sets arranged on the first end, the two fixation sets comprising:
    two upper parts which are adapted to be attached to both ends of a bridge element which forms a matrix support; and two lower parts which are adapted to be mounted on two end portions of a head ring forming the patient holder, wherein:

one of the two lower parts and two upper parts comprise two longitudinally extending co-extending rails, and another of the two lower parts and the two upper parts comprise two longitudinally extending rail-engaging profiles, the two longitudinally extending co-extending rails and the two longitudinally extending rail-engaging profiles being formed so as to allow the upper parts being placed onto the lower parts covered by the sterile drape in a direction that is perpendicular to an extension of the two longitudinally extending co-extending rails, the two longitudinally extending co-extending rails and the longitudinally extending rail-engaging profiles being formed to accommodate and clamp the sterile drape between them without penetrating the sterile drape.

19. A fixation system for attaching a medical image registration matrix to a patient holder which is to be covered by a sterile drape and has first and second ends opposite one another, wherein the fixation system comprises two fixation sets, wherein one of the two fixation sets is arranged on the first end of the patient holder and another of the two fixation sets is arranged on the second end of the patient holder laterally spaced from the one of the two fixation sets arranged on the first end, wherein each fixation set comprises:

an upper part adapted to be attached to one end of a bridge element that fours a matrix support; and a lower part adapted to be mounted on an end portion of a head ring forming the patient holder, wherein each lower part comprises a longitudinally extending co-extending rail and each upper part comprises a longitudinally extending rail-engaging profile, wherein each upper part is configured to be placed onto one of the lower parts in a direction that is perpendicular to an extension of the respective longitudinally extending co-extending rail when each lower part is covered by the sterile drape, and wherein each upper part and each lower part is formed to accommodate and clamp the sterile drape between them without penetrating the sterile drape.

* * * * *

UNITED STATES PATENT AND TRADEMARK OFFICE
CERTIFICATE OF CORRECTION

PATENT NO.        : 9,943,369 B2
APPLICATION NO.   : 14/000529
DATED             : April 17, 2018
INVENTOR(S)       : Rupert Heigl et al.

It is certified that error appears in the above-identified patent and that said Letters Patent is hereby corrected as shown below:

In the Claims

Column 10, Line 8:
--that fours--
Should read:
--that forms--

Signed and Sealed this
Fifth Day of June, 2018

Andrei Iancu
*Director of the United States Patent and Trademark Office*